United States Patent [19]

Neunhoeffer et al.

[11] Patent Number: 5,430,159
[45] Date of Patent: Jul. 4, 1995

[54] N-PHENYLAMINOPYRAZOLE DERIVATIVES AS WELL AS COMPOSITION AND PROCESS FOR THE DYEING OF HAIR

[75] Inventors: Hans Neunhoeffer, Mühltal; Stefan Gerstung, Reinheim; Thomas Clausen; Wolfgang R. Balzer, both of Alsbach, all of Germany

[73] Assignee: Wella Aktiengesellschaft, Darmstadt, Germany

[21] Appl. No.: 244,069

[22] Filed: May 9, 1994

[30] Foreign Application Priority Data

Oct. 16, 1992 [DE] Germany .............. 42 34 886.2

[51] Int. Cl.⁶ .................. A61K 7/13; C09B 57/00
[52] U.S. Cl. .................... 548/371.4; 8/416
[58] Field of Search ............ 548/371.4; 8/416

[56] References Cited

U.S. PATENT DOCUMENTS 4,803,216  2/1989  Appleton et al. ............ 548/371.4
5,061,289  10/1991  Clausen et al. ............ 8/416

FOREIGN PATENT DOCUMENTS 2234476  1/1973  Germany .
2234525  1/1983  Germany .

*Primary Examiner*—Robert W. Ramsuer
*Attorney, Agent, or Firm*—Michael J. Striker

[57] ABSTRACT

The hair dye composition includes at least one N-phenylaminopyrazole compound of the formula (V)

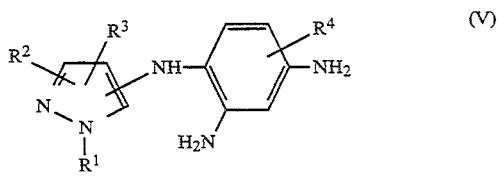

wherein $R^1$ is hydrogen, an alkyl group having from one to four carbon atoms or a hydroxyalkyl group having from two to four carbon atoms; $R^2$ and $R^3$ are each independently either a hydrogen, an amino groups or an alkyl group having from one to four carbon atoms; and $R^4$ is hydrogen, an alkyl group having from one to four carbon atoms, an alkoxy group having from one to four carbon atoms or a halogen; and at least one conventional ingredient for hair dye compositions selected from the group consisting of emollients; preservatives; perfume oils; solvents; anionic, cationic, amphoteric and nonionic surfactants; thickeners; starch derivatives; cellulose derivatives; petrolatum; paraffin oil; fatty acids; conditioners; lanolin derivatives; cholesterol; pantothenic acid and betaines.

12 Claims, No Drawings

N-PHENYLAMINOPYRAZOLE DERIVATIVES AS WELL AS COMPOSITION AND PROCESS FOR THE DYEING OF HAIR

BACKGROUND OF THE INVENTION

The present invention relates to new substituted N-phenylaminopyrazoles and to hair dye compositions containing these compounds and to a process for dyeing hair.

It is already known to use leuco derivatives of indoaniline for dyeing hair. These colorless compounds are applied to the fibers to be dyed in aqueous solution and oxidized by air or some other oxidant to form indoanilines which are colored compounds. Due to the good solubility of leuco compounds the dyes obtained in this way have intensity and fastness properties which are superior to those of dyeing obtained by direct application of indoanilines. For example, German Patent applicatons DE-OS 22 34 525 and DE-OS 22 34 476 describe leuco derivatives of these compounds. However, the dyeing intensities which can be achieved with these leuco derivatives are unsatisfactory.

SUMMARY OF THE INVENTION

Therefore, it is an object of the present invention to provide new leuco compounds which can be converted to dyes of high intensity and good fastness properties by oxidation.

It has now been found that the proposed object of the present invention is attained in an outstanding manner by the N-phenylaminopyrazole derivatives of the general formula (I)

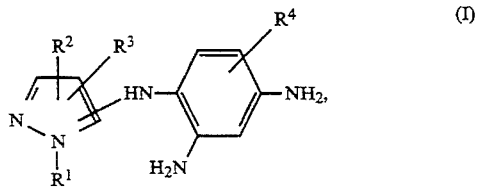

where $R^1$ is hydrogen, $C_1$- to $C_4$-alkyl or $C_2$- to $C_4$-hydroxyalkyl, $R^2$ and $R^3$ can be identical or different and are hydrogen, an amino- or $C_1$- to $C_4$-alkyl radical, and $R^4$ is hydrogen, $C_1$- to $C_4$alkyl, halogen or $C_1$- to $C_4$-alkoxy with the proviso that, if $R^1$ is hydrogen or an alkyl group having from one to four carbon atoms, at least one of $R^2$ and $R^3$ is an amino group. The compounds of formula (I) are therefore the subject matter of the invention.

The compounds of formula (I) can be produced in a simple manner by coupling aminopyrazoles of the general formula (II), in which $R^1$ has the same meaning as indicated in the preceding and $R^a$ and $R^b$ are hydrogen, a $C_1$- to $C_4$-alkyl radical or a nitro group with substituted dinitro halogen benzenes (III) and subsequent reduction of the obtained (2',4'-dinitrophenylamino)-pyrazoles (IV).

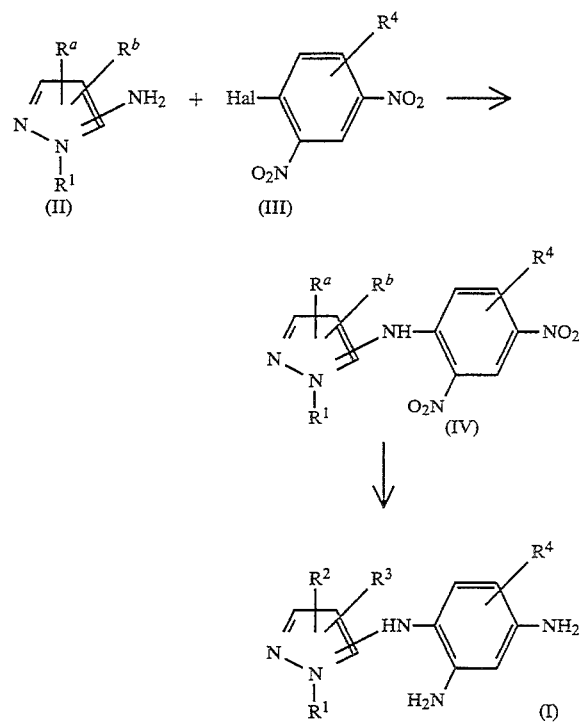

The following are examples of suitable N-phenylaminopyrazoles of formula (I):
5-amino-4-(2',4'-diaminophenylamino)-1-methylpyrazole,
4-amino-5-(2',4'-diaminophenylamino )-1-methylpyrazole,
3-amino-4-(2',4'-diaminophenylamino )-1-methylpyrazole.

After oxidation, the new compounds of formula (I) produce dyes with high color intensity and good fastness or permanency properties, in particular with respect to light, rubbing and washing. Therefore, further subject matter of the present application is a hair dye composition containing conventional ingredients for hair dye compositions which is characterized in that it contains at least one N-phenylaminopyrazole derivative of the general formula (V).

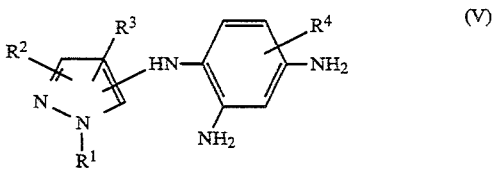

wherein $R^1$ is a substituent member selected from the group consisting of hydrogen, alkyl groups having from one to four carbon atoms, hydroxyalkyl groups having from two to four carbon atoms; $R^2$ and $R^3$ are each a substituent group independently selected from the group consisting of hydrogen, amino groups and alkyl groups having from one to four carbon atoms; and $R^4$ is a substituent group selected from the group consisting of hydrogen, alkyl groups having from one to four carbon atoms, alkoxy groups having from one to four carbon atoms and halogen; and at least one conventional ingredient for hair dye compositions as set forth hereinbelow.

The compounds of general formula (V) are contained in the composition according to the invention in concentrations of 0.001 to 2 percent by weight, preferably in concentrations of 0.01 to 0.5 percent by weight, where the compounds of general formula (V) may also be present in the form of their physiologically tolerated, water-soluble salts.

The hair dye composition according to the invention is a composition containing at least one dye of the general formula (V) or a composition which, in addition to at least one dye of the general formula (V), contains one or more dyes conventionally used in hair dye compositions.

Examples of such dyes are: oxidative dyes such as p-phenylenediamine derivatives or m-phenylenediamine derivatives, p-aminophenol derivatives or m-aminophenol derivatives and resorcinol and its derivatives or direct dyes such as aromatic nitro dyes, triphenylmethane dyes, azo dyes and anthraquinone dyes.

The hair dye composition according to the invention can be in the form of a solution, e.g. an aqueous or aqueous-alcoholic solution, an emulsion, cream or gel.

This hair dye composition has a pH value between 4 and 11, preferably from 6 to 9. The desired alkaline pH is adjusted with ammonia, organic amines, e.g. monoethanolamine, or caustic soda, while phosphoric acid or organic acids such as acetic acid, tartaric acid or citric acid can be used to adjust an acidic pH.

Of course, the additional conventional ingredients for hair dye compositions include emollients, preservatives and perfume oils, solvents such as water, lower aliphatic alcohols such as ethanol, propanol and isopropanol or glycols such as glycerin and 1,2-propylene glycol, as well as wetting agents or emulsifiers from the classes oranionic, cationic, amphoteric or nonionic surface-active substances such as fatty alcohol sulfates, ethoxylated fatty alcohol sulfates, alkyl sulfonates sulfates, alkyl benzene sulfonates, alkyl trimethyl ammonium salts, alkyl betaines, ethoxylated fatty alcohols, ethoxylated nonylphenols, fatty acid alkanolamides, ethoxylated fatty acid esters, and thickeners such as higher fatty alcohols, starch or cellulose derivatives, also petrolatum, paraffin oil and fatty acids, as well as conditioners such as cationic resins, tanolin derivatives, cholesterol, pantothenic acid and betaine. The aforementioned ingredients are used in the usual amounts required for such purposes, e.g. the wetting agents and emulsifiers are used in concentrations of approximately 0.5 to 30 percent by weight, the thickeners in quantities of approximately 0.1 to 25 percent by weight and the conditioners in concentrations of approximately 0.1 to 5.0 percent by weight.

The dyeing of hair by the hair dye composition according to the invention is effected in a conventional manner by applying an amount (60 to 200 g) of the composition to the hair sufficient for dyeing the hair and allowing it to remain in contact with the hair for a period of 10 to 30 minutes. The hair is then rinsed with water and dried.

The hair dye composition according to the invention can also be mixed with an oxidant such as hydrogen peroxide or its addition compounds, e.g. urea peroxide or carbamide peroxide, prior to application and then applied in the manner indicated above.

The following examples will serve to explain the subject matter of the present invention in more detail without limiting it to these examples.

PRODUCTION EXAMPLES

Example 1

Synthesis of (2',4'-dinitrophenylamino)pyrazoles

A. General directions for converting aminopyrazoles with 2,4dinitrochlorobenzenes or 2,4-dinitroiodobenzenes The indicated amount ofaminopyrazole is dissolved in 50 ml absolute acetonitrile or ethanol and mixed with the appropriate amount of a possibly substituted 2,4-dinitrochlorobenzene or 2,4-dinitroiodobenzene. This mixture is heated to boiling for 2 hours, whereupon an equimolar amount of potassium hydroxide powder or ammonia is added and the mixture allowed to react at boiling temperature for another 2 to 4 hours. The solvent is then evaporated and the residue is absorbed in 100 ml water and extracted three times with 100 ml acetic acid in each instance. After drying over magnesium sulfate, it is evaporated and chromatographed on silica gel with ether.

I. Synthesis of 4-(2',4'-dinitrophenylamino)-1-methyl-5-nitropyrazole 100 mg (0.70 mmoles) 4-amino-1-methyl-5-nitropyrazole are converted in acetonitrile with 210 mg (0.70 mmoles) 2,4-dinitroiodobenzene according to the foregoing general directions. After 2 hours, 40 mg (0.70 mmoles) of potassium hydroxide are added.

Yield: 120 mg (55 percent of theory) 4-(2',4'-dinitrophenylamino)-1-methyl-5-nitropyrazole are obtained as orange crystals with a melting point of 156 degrees Celsius (ether).

60 MHz-$^1$H-NMR ([D$_6$]DMSO):

$\delta=10.78$ ppm (s, wide, 1H, NH, exchangeable with D$_2$O), 8.92 ppm (d, J=2 Hz, 1H, 3'-H), 8.36 ppm (dd, J$^1$=10 Hz, J$^2$=2 Hz, 1H, 5'-H), 8.13 ppm (s, 1H, 3-H), 7.65 ppm (d, J=10 Hz, 1H, 6'-H) and 4.20 ppm (s, 3H, CH$_3$)

MS (70 ev) m/e: 308 [M+].

II. Synthesis of 5-(2',4'-dinitrophenylamino)-1-methyl-4-nitropyrazole

According to the foregoing general directions, 0.55 g (3.87 mmoles) 5-amino-1-methyl-4-nitropyrazole are converted and worked up with 1.14 g (3.87 mmoles) 2,4-dinitroiodobenzene and 210 mg (3.87 mmoles) potassium hydroxide.

Yield: 0.65 g (55 percent of theory) 5-(2',4'-dinitrophenylamino)-1-methyl-4-nitropyrazole are obtained as bright-yellow crystals with a melting point of 182 degrees Celsius (ether).

60 MHz-$^1$-NMR ([D$_6$]DMSO):

$\delta=10.19$ ppm (s, wide, 1H, NH, exchangeable with D$_2$O), 8.93 ppm (d, J=2 Hz, 1H, 3'-H), 8.42 ppm (s, 1H, 3-H), 8.25 ppm (dd, J$^1$=10 Hz, J$^2$=2 Hz, 1H, 5'-H), 6.95 ppm (d, J=10 Hz, 1H, 6'-H) and 3.80 ppm (s, 3H, CH$_3$)

MS (70 ev) m/e: 308 [M+].

III. Synthesis of 4-(2',4'-dinitrophenylamino)-1-methyl-3-nitropyrazole

Corresponding to the general directions, 100 g (0.70 mmoles) 4-(2',4'-dinitrophenylamino)-1-methyl-3-nitropyrazole are convened and worked up with 210 mg (0.70 mmoles) 2,4-dinitroiodobenzene and 40 mg (0.70 mmoles) potassium hydroxide.

Yield: 130 mg (60 percent of theory) 4-(2',4'-dinitrophenylamino)-1-methyl-3-nitropyrazole are obtained as orange crystals with a melting point of 195 degrees Celsius (ether).

60 MHz-$^1$H-NMR ([D$_6$]DMSO):

$\delta = 10.63$ ppm (s, wide, 1H, NH, exchangeable with D$_2$O), 8.92 ppm (d, J=2 Hz, 1H, 3'-H), 8.49 ppm (s, 1H, 3-H), 8.30 ppm (dd, J$^1$=10 Hz, J$^2$=2 Hz, 1H, 5'-H), 7.46 ppm (d, J=10 Hz, 1H, 6'-H) and 4.03 ppm (s, 3H, CH$_3$)

MS (70 ev) m/e: 308 [M+].

IV. Synthesis of 3-(2',4'-dinitrophenylamino)-1-methylpyrazole

Corresponding to the general directions, 200 g (20.6 mmoles) 3-amino-1-methylpyrazole are converted and worked up with 4.17 g (20.6 mmoles) 2,4-dinitrochlorobenzene and 1.15 g (20.6 mmoles) potassium hydroxide.

Yield: 3.20 g (59 percent of theory) 3-(2',4'-dinitrophenylamino)-1-methylpyrazole are obtained as red needles with a melting point of 150 degrees Celsius (ethylacetate).

60 MHz-$^1$H-NMR ([D$_6$]DMSO):

$\delta = 10.15$ ppm (s, wide, 1H, NH, exchangeable with D$_2$O), 8.84 ppm (d, J=3 Hz, 1H, 3'-H), 8.33 ppm (dd, J$^1$=10 Hz, J$^2$=3 Hz, 1H, 5'-H), 8.03 ppm (d, J=10 Hz, 1H, 6'-H), 7.77 ppm (d, J=2 Hz, 1H, 5-H), 6.26 ppm (d, J=2 Hz, 1H, 4-H) and 3.85 ppm (s, 3H, CH$_3$)

MS (70 ev) m/e: 263 [M+].

V. Synthesis of 4-(2',4-dinitrophenylamino)-1-methylpyrazole

A solution of 0.50 g (5.15 mmoles) 4-amino-1-methylpyrazole in 50 ml acetonitrile (or ethanol) is mixed with 2.00 g (9.90 mmoles) 2,4-dinitrochlorobenzene and heated to boiling for 2 hours. After adding 5 ml concentrated ammonia, it is heated for another 2 hours to boiling accompanied by stirring. When cooled, the product precipitates out. It is removed by suction, washed with water and dried in a vacuum.

Yield: 0.64 g (47 percent of theory)4-(2',4'-dinitrophenylamino)-1-methylpyrazole are obtained as red needles with a melting point of 149 degrees Celsius (ethanol).

60 MHz-$^1$H-NMR ([D$_6$]DMSO):

$\delta = 9.72$ ppm (s, wide, 1H, NH, exchangeable with D$_2$O), 8.82 ppm (d, J=3 Hz, 1H, 3'-H), 8.20 ppm (dd, J$^1$=10 Hz, J$^2$=3 Hz, 1H, 5'-H), 7.93 ppm (s, 1H, 5-H), 7.53 ppm (s, 1H, 3-H), 7.15 ppm (d, J=10 Hz, 1H, 6'-H) and 3.90 ppm (s, 3H, CH$_3$)

MS (70 ev) m/e: 263 [M+].

VI. Synthesis of 5-(2', 4'-dihenylaminphenylamino)-1-methylpyrazole

Corresponding to the general directions, 1.60 g (16.5 mmoles) 5-amino-1-methylpyrazole are converted and worked up with 3.34 g (16.5 mmoles) 2,4-dinitrochlorobenzene and 0.90 g (16.5 mmoles) potassium hydroxide.

Yield: 1.52 g (35 percent of theory) 5-(2',4'-dinitrophenylamino)-1-methylpyrazole are obtained as yellow crystals with a sublimation point of 175 degrees Celsius (ether).

60 MHz-$^1$H-NMR ([D$_6$]DMSO):

$\delta = 9.95$ ppm (s, wide, 1H, NH, exchangeable with D$_2$O), 8.90 ppm (d, J=3 Hz, 1H, 3'-H), 8.30 ppm (dd, J$^1$=10 Hz, J$^2$=3 Hz, 1H, 5'-H), 7.57 ppm (d, J=2 Hz, 1H, 1H, 3-H), 6.83 ppm (d, J=10 Hz, 1H, 6'-H), 6.31 ppm (d, J=2 Hz, 1H, 4-H) and 3.69 ppm (s, 3H, CH$_3$)

MS (70 ev) m/e: 263 [M+].

VII. Synthesis of 4-(2',4'-dinitrophenylamino)-1,3,5-trimethylpyrazole 1.00 g (4.15 mmoles) 4-amino-1,3,5-trimethylpyrazole hydrosulfate hydrate are mixed in 50 ml ethanol with 10 ml concentrated ammonia and 1.26 g (6.22 mmoles) 2,4-dinitrochlorobenzene and heated to boiling for 2 hours. The preparation is effected corresponding to the general directions.

Yield: 0.87 g (72 percent of theory) 4-(2',4'-dinitrophenylamino)-1,3,5-trimethylpyrazole are obtained as orange crystals with a melting point of 153 degrees Celsius (ether).

60 MHz-$^1$H-NMR ([D$_6$]DMSO):

$\delta = 9.60$ ppm (s, wide, 1H, NH, exchangeable with D$_2$O), 8.89 ppm (d, J=3 Hz, 1H, 3'-H), 8.81 ppm (dd, J$^1$=10 Hz, J$^2$=3 Hz, 1H, 5'-H), 6.77 ppm (d, J=10 Hz, 1H, 6'-H), 3.72 ppm (s, 3H, 1-NCH$_3$), 2.10 ppm (s, 3H, 3(5)-CH$_3$) and 1.97 ppm (s, 3H, 5(3)-CH$_3$)

MS (70 ev) m/e: 291 [M+].

Example 2

Synthesis of (2',4'-diaminophenylamino)pyrazoles

A: General directions for hyration in sulfuric acid

The indicated amount of nitropyrazole in a solution of an equimolar amount of concentrated sulfuric acid in 25 ml water is mixed with 100 mg palladium/activated charcoal catalyst and hydrated at normal pressure and room temperature accompanied by vigorous shaking in a hydrating flask for 2 to 6 hours. To speed up the reaction of substances with very poor solubility, 5 ml ethanol are added to the reaction mixture. At the conclusion of the reaction the catalyst is removed by suction in a nitrogen atmosphere and the mother liquor is evaporated until dry. The residue is mixed with 5 ml absolute ethanol accompanied by formation of crystals. The product is removed by suction, washed with ethanol and dried in a vacuum.

I. Synthesis of 5-amino-4-(2',4'-diaminophenylamino)-1-methylpyrazole 100 mg (0.33 mmoles) 4-(2',4'-dinitrophenylamino)-1-methyl-5-nitropyrazole are hydrated in a solution of 35 mg (0.33 mmoles) concentrated sulfuric acid in 25 ml water for 4 hours.

Yield: 90 mg (87 percent of theory) 5-amino-4-(2',4'-diaminophenylamino)-1-methylpyrazole hydrosulfate are obtained as colorless crystals with a decomposition point of 165 degrees Celsius (ethanol).

II. Synthesis of 4-amino-5-(2',4'diaminophenylamino)-1-methylpyrazole 0.50 g (1.62 mmoles) 5-(2',4'-dinitrophenylamino)-1-methyl-4-nitropyrazole are hydrated in a solution of 165 mg( 1.62 mmoles) concentrated sulfuric acid in 50 ml water.

Yield: 340 mg (45 percent of theory) 4-amino-5-(2',4'-diaminophenylamino)-1methylpyrazole dihydrosulfate trihydrate are obtained as black crystals with a decomposition point of 170 degrees Celsius (ethanol).
300 MHz-$^1$H-NMR, ([D$_6$]DMSO/D$_2$O):

δ=7.39 ppm (s, 1H, 3-H)
6.55 ppm (s, 1 H, 3'-H),
6.32 ppm (d, J=8.0 Hz, 1H, 5'-H),
6.07 ppm (d, J=8.0 Hz, 1H, 6'-H),
4.92 ppm (s, wide, 17H, NH, NH$_2$, H$_2$SO$_4$, H$_2$O) and
3.44 ppm (s, 3 H, CH$_3$)
MS (70 ev) m/e: 218 [M+].

III. Synthesis of 3-amino-4-(2',4'-diaminophenylamino)-1-methylpyrazole 70 ml (0.23 mmoles) 4-(2',4'-dinitrophenylamino)-1-methyl-3-nitropyrazole are hydrated in a solution of 25 mg (0.23 mmoles) concentrated sulfuric acid in 20 ml water.

Yield: 55 mg (97 percent of theory)3-amino-4-(2',4'-diaminophenylamino)-1-methylpyrazole hydrosulfate are obtained as colorless, hygroscopic crystals with a decomposition point of 168 degrees Celsius (ethanol).

IV. Synthesis of 3-(2',4'-diaminophenylamino)-1-methylyprazole 1.00 g (3.80 mmoles) 3-(2',4'-dinitrophenylamino)-1-methylpyrazole are hydrated in a solution of 380 mg (3.80 mmoles) concentrated sulfuric acid in 50 ml water.

Yield: 0.57 g (50 percent of theory) 3-(2',4'-diaminophenylamino)- 1-methylpyrazole hydrosulfate are obtained as colorless, hygroscopic crystals with a decomposition point of 152 degrees Celsius (ethanol).
MS (70 eV) m/e: 203 [M+].

V. Synthesis of 4-(2', 4'-diaminophenylamino)-1-methlpyrazole 0.50 g (1.90 mmoles) 4-(2',4'-dinitrophenylamino)-1-methylpyrazole are hydrated in a solution of 190 mg (1.90 mmoles) concentrated sulfuric acid in 30 ml water.

Yield: 0.39 g (69 percent of theory) 4-(2', 4'-diaminophenylamino)-1-methylpyrazole hydrosulfate are obtained as beige, hygroscopic crystals with a decomposition point of 162 to 164 degrees Celsius (ethanol).
MS (70 eV)m/e: 203 [M+].

VI. Synthesis of 5-(2', 4'-diaminophenylamino)-1-methylpyrazole 140 mg (0.53 mmoles) 5-(2',4'-dinitrophenylamino)-1-methylpyrazole are hydrated in a solution of 55 mg (0.53 mmoles) concentrated sulfuric acid in 20 ml water.

Yield: 100 mg (63 percent of theory) 5-(2',4'-diaminophenylamino)-1-methylpyrazole hydrosulfate are obtained as colorless, hygroscopic crystals with a decomposition point of 183 degrees Celsius (ethanol).
MS (70 eV) m/e: 203 [M+].

VII. Synthesis of 4(2',4'-diaminophenylamino)-1,3,5-trimethylpyrazole 400 mg (1.37 mmoles) 4-(2',4'-dinitrophenylamino)-1,3,5-trimethylpyrazole are hydrated in a solution of 140 mg (1.37 mmoles) concentrated sulfuric acid in 20 ml water.

Yield: 380 mg (84 percent of theory)4-(2',4'-diaminophenylamino)-1,3,5-trimethylpyrazole hydrosulfate are obtained as colorless, hygroscopic crystals with a decomposition point of 165 degrees Celsius (ethanol).
MS (70 eV) m/e: 231 [M+].

For all NMR spectra: s=singlet, d=doublet.

HAIR DYE EXAMPLES

Examples 3 to 9

Hair dye solutions having the following composition were produced:

2.50 g dye according to Examples 2/I to VII
10.00 g lauryl alcohol diglycol ether sulfate sodium salt (28-percent aqueous solution)
87.50 g water
100.00 g The hair dye solutions were applied to graying human hair and allowed to act at 40 degrees Celsius for 30 minutes. The hair was rinsed with water and dried. The resulting colorings are shown in Table 1.

TABLE 1

| Example | Dye from Example | Color |
|---------|------------------|-------|
| 3 | 2/I | bright violet |
| 4 | 2/II | brown |
| 5 | 2/III | violet |
| 6 | 2/IV | reddish brown |
| 7 | 2/V | reddish brown |
| 8 | 2/VI | reddish brown |
| 9 | 2/VII | brown |

All percentages indicated in the present patent application represent percent by weight unless otherwise noted.

We claim:

1. N-phenylaminopyrazole compound of the formula (I)

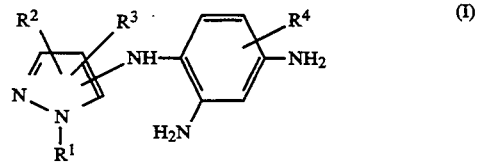

wherein R$^1$ is a substituent group selected from the group consisting of hydrogen, alkyl groups having from one to four carbon atoms and hydroxyalkyl groups having from two to four carbon atoms; R$^2$ and R$^3$ are each a substituent group independently selected from the group consisting of hydrogen, amino groups and alkyl groups having from one to four carbon atoms; and R$^4$ is a substituent group selected from the group consisting of hydrogen, alxyl groups having from one to four carbon atoms, alkoxy groups having from one to four carbon atoms and halogen; with the proviso that, if said R$^1$ is a member of the group consisting of hydrogen and alkyl groups having from one to four carbon atoms, at least one of said R$^2$ and R$^3$ is one of said amino groups.

2. N-phenylaminopyrazole compound as defined in claim 1 and consisting of 5-amino-4-(2',4'-diaminophenylamino)-1-methylpyrazole.

3. N-phenylaminopyrazole compound as defined in claim 1 and consisting of 4-amino-5-(2',4'-diaminophenylamino)-1-methylpyrazole.

4. N-phenylaminopyrazole compound as defined in claim 1 and consisting of 3-amino-4-(2',4'-diaminophenyylamino)-1-methylpyrazole.

5. Hair dye composition comprising at least one N-phenylaminopyrazole compound of the formula (I)

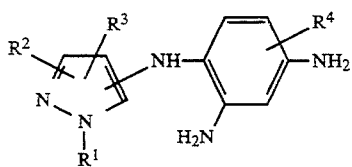

wherein $R^1$ is a substituent member selected from the group consisting of hydrogen, alkyl groups having from one to four carbon atoms, hydroxyalkyl groups having from two to four carbon atoms; $R^2$ and $R^3$ are each a substituent group independently selected from the group consisting of hydrogen, amino groups and alkyl groups having from one to four carbon atoms; and $R^4$ is a substituent group selected from the group consisting of hydrogen, alkyl groups having from one to four carbon atoms, alkoxy groups having from one to four carbon atoms and halogen, with the proviso that, if said $R^1$ member of the group consisting of hydrogen and alkyl groups having from one to four carbon atoms, at least one of said $R^2$ and $R^3$ is one of said amino groups;

and at least one conventional ingredient for hair dye compositions selected from the group consisting of emollients; preservatives; perfume oils; solvents; anionic, cationic, amphoteric and nonionic surfactants; thickeners; starch derivatives; cellulose derivatives; petrolatum; paraffin oil; fatty acids; conditioners; lanolin derivatives; cholesterol; pantothenic acid and betaines.

6. Hair dye composition as defined in claim 5 and containing 0,001 to 2 percent by weight of said at least one N-phenylaminopyrazole compound of the formula (V).

7. Hair dye composition as defined in claim 5 and having a pH of from 4 to 11.

8. Hair dye composition as defined in claim 5 in the form of an aqueous or aqueous-alcoholic solution, an emulsion, a cream or a gel.

9. Hair dye composition as defined in claim 5, further comprising at least one oxidation hair dye.

10. Hair dye composition as defined in claim 5, further comprising at least one direct dye for direct absorption on hair to be dyed.

11. Process for dyeing hair comprising the steps of:
a) providing a hair dye composition comprising at least one N-phenylaminopyrazole compound of the formula (v)

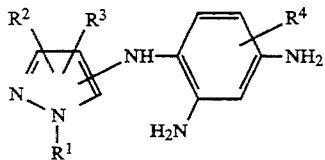

wherein $R^1$ is a substituent member selected from the group consisting of hydrogen, alkyl groups having from one to four carbon atoms, hydroxyalkyl groups having from two to four carbon atoms; $R^2$ and $R^3$ are each a substituent group independently selected from the group consisting of hydrogen, amino groups and alkyl groups having from one to four carbon atoms; and $R^4$ is a substituent group selected from the group consisting of hydrogen, alkyl groups having from one to four carbon atoms, alkoxy groups having from one to four carbon atoms and halogen; and at least one conventional ingredient for hair dye compositions selected from the group consisting of emollients; preservatives; perfume oils; solvents; anionic, cationic, amphoteric and nonionic surfactants; thickeners; starch derivatives; cellulose derivatives; petrolatum; paraffin oil; fatty acids; conditioners; lanolin derivatives; cholesterol; pantothenic acid and betaines;

b) applying an amount of said hair dye composition to the hair;

c) allowing said hair dye composition to act on the hair for from 10 to 30 minutes, and d) subsequent to step c), rinsing said hair dye composition from the hair and drying the hair.

12. Process for dyeing hair comprising the steps of:
a) providing a hair dye composition comprising at least one N-phenylaminopyrazole compound of the formula (V)

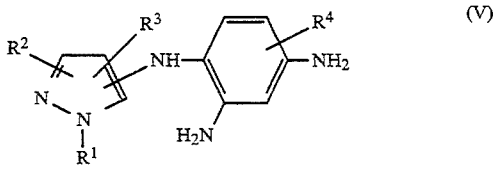

wherein $R^1$ is a substituent member selected from the group consisting of hydrogen, alkyl groups having from one to four carbon atoms, hydroxyalkyl groups having from two to four carbon atoms; $R^2$ and $R^3$ are each a substituent group independently selected from the group consisting of hydrogen, amino groups and alkyl groups having from one to four carbon atoms; and $R^4$ is a substituent group selected from the group consisting of hydrogen, alkyl groups having from one to four carbon atoms, alkoxy groups having from one to four carbon atoms and halogen; and at least one conventional ingredient for hair dye compositions selected from the group consisting of emollients; preservatives; perfume oils; solvents; anionic, cationic, amphoteric and nonionic surfactants; thickeners; starch derivatives; cellulose derivatives; petrolatom; paraffin oil; fatty acids; conditioners; lanolin derivatives; cholesterol; pantothenic acid and betainca;

b) prior to applying to hair, mixing an oxidizing agent with an amount of said hair dye composition to form a hair dyeing mixture;

c) applying said hair dye mixture to the hair;

d) allowing said hair dye mixture to act on the hair for from 10 to 30 minutes, e) subsequent to step d), rinsing said hair dye composition from the hair and drying the hair.

* * * * *